United States Patent [19]

Sarantakis

[11] 4,011,182
[45] Mar. 8, 1977

[54] CYCLIC UNDECAPEPTIDE ANALOGS OF SOMATOSTATIN AND INTERMEDIATES

[75] Inventor: Dimitrios Sarantakis, West Chester, Pa.

[73] Assignee: American Home Products Corporation, New York, N.Y.

[22] Filed: Dec. 10, 1975

[21] Appl. No.: 639,550

Related U.S. Application Data

[63] Continuation-in-part of Ser. No. 560,671, March 21, 1975, abandoned.

[52] U.S. Cl. ..................................... 260/8; 260/6; 260/112.5 S; 424/177
[51] Int. Cl.² ............... C07C 103/52; A61K 37/00; C08L 25/06
[58] Field of Search ..................... 260/112.5 S, 8, 6

[56] References Cited

UNITED STATES PATENTS 3,904,594   9/1975   Guillemin et al. ........... 260/112.5 S Primary Examiner—Lewis Gotts
Assistant Examiner—Reginald J. Suyat
Attorney, Agent, or Firm—Richard K. Jackson

[57] ABSTRACT

Cyclic undecapeptide analogs of somatostatin without cysteine amino acid residues and intermediates obtained in the synthesis of such compounds are described. These cyclic undecapeptides inhibit the secretion of the hormone somatotropin (growth hormone) without materially affecting glucagon levels.

15 Claims, No Drawings

CYCLIC UNDECAPEPTIDE ANALOGS OF SOMATOSTATIN AND INTERMEDIATES

RELATED APPLICATION

This application is a continuation-in-part of Ser. No. 560,671, filed Mar. 21, 1975, now abandoned.

This invention relates to cyclic undecapeptide analogs of somatostatin and intermediates obtained in their synthesis by a combination of the solid phase and classical method of peptide synthesis.

Somatostatin (also known as somatotropin release inhibiting factor or SRIF) is the tetradecapeptide

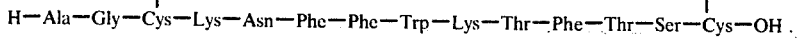

This tetradecapeptide has been identified by isolation from extracts of ovine hypothalamic tissues and found to inhibit the secretion of the hormone somatotropin which is commonly referred to as the growth hormone (GH); See Brazeau et al., Science, 179 pp 77–79 (January 1973). The linear form of this tetradecapeptide, H-Ala-Gly-Cys-Lys-Asn-Phe-Phe-Trp-Lys-Thr-Phe-Thr-Ser-Cys-OH, has also been reported by Brazeau et al., supra, to have been synthesized by solid phase methodology and found to have the same biological activity as the somatostatin obtained from a natural source. In copending application Ser. No. 430,441 filed Jan. 3, 1974, now U.S. Pat. No. 3,882,098, the undecapeptide Des-Ala$^1$-Gly$^2$-Asn$^5$-SRIF and its oxidized form are described and in copending application Ser. No. 457,038 filed Apr. 1, 1974, the dodecapeptide Des-Ala$^1$-Gly$^2$-SRIF and it oxidized form are described.

Cyclic analogs of somatostatin not contained cysteine have not been reported in the prior art. Thus, the cyclic undecapeptides of the present invention possess a cyclic structure which contains not sulfur but carbon as a ring member and also eliminates the amino acids from the one and two positions of somatostatin (i.e. Ala and Gly).

The cyclic undecapeptides of the present invention which inhibit the secretion of the hormone somatotropin are represented by the formula

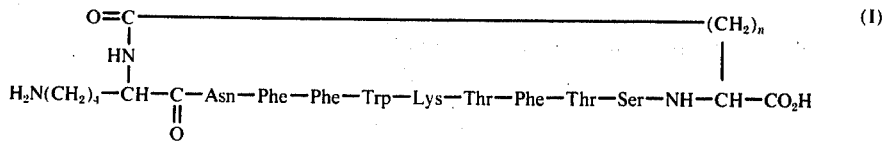

in which Trp represents either D- or L-tryptophyl and all the other amino acids are of the L-configuration and the non-toxic acid addition salts thereof; and wherein $n$ is a whole number from 1 through 5; where $n=1$ the C-terminal amino acid is aspartic acid; where $n=2$ the C-terminal amino acid is glutamic acid; where $n=3$ the C-terminal amino acid is α-aminoadipic acid; where $n=4$ the C-terminal amino acid is α-aminopimelic acid; and where $n=5$ the C-terminal amino acid is α-aminosuberic acid. The preferred compound of formula I is one in which $n=2$.

Illustrative of acid addition salts are hydrochloride, hydrobromide, sulfate, phosphate, maleate, acetate, citrate, benzoate, succinate, malate, ascorbate and the like.

The nomenclature used to depict the peptides follows that adopted by Schroder & Lubke, "The Peptides," 1, pp viii–xxix (Academic Press 1965). All chiral amino acid residues identified in formula I and the other formulas hereinafter are of the natural or L-configuration, except for Trp, which is optionally of the L- or D-configuration.

The present invention also relates to novel decapeptide intermediates of the formula:

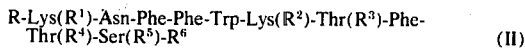

wherein:

R is an α-amino protecting group. The α-amino protecting groups contemplated by R are those known to be useful in the art in the step-wise synthesis of polypeptides. Among the classes of α-amino protecting groups covered by R are (1) acyl type protecting groups illustrated by the following: formyl, trifluoroacetyl, phthalyl, toluenesulfonyl (tosyl), benzenesulfonyl, nitrophenylsulfenyl, tritylsulfenyl, O-nitrophenoxyacetyl, γ-chlorobutyryl, etc; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methyoxybenzyloxycarbonyl, 1-(p-biphenylyl)-1-methylethoxycarbonyl, α,α-dimethyl-3,5-dimethoxybenzyloxycarbonyl and benzhydryloxycarbonyl, (3) aliphatic urethan protecting groups illustrated by tert-butyloxycarbonyl, diisopropylmethoxycarbonyl, isopropyloxycarbonyl, ethoxycarbonyl, allyloxycarbonyl; (4) cycloalkyl urethan type protecting groups illustrated by cyclopentyloxycarbonyl, adamantyloxycarbonyl, cyclohexyloxycarbonyl; (5) thio urethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting group defined by R is tert-butyloxycarbonyl;

R$^1$ is a protecting group for the side chain amino substituent of lysine. Illustrative of suitable side chain amino protecting groups are benzyloxycarbonyl and substituted benzyloxycarbonyl said substituent being selected from halo (e.g. chloro, bromo, fluoro) and nitro (e.g. 2-chlorobenzyloxycarbonyl, p-nitrobenzyloxycarbonyl, 3,4-dichlorobenzyloxycarbonyl), tosyl, t-amyloxycarbonyl, t-butyloxycarbonyl, diisopropylmethoxycarbonyl; etc. The selection of such a side chain amino protecting group is not critical except that it must be one which is not removed during cleavage of the α-amino protecting group during the synthesis until the cyclic undecapeptide of the desired amino acid sequence is obtained. Hence, the α-amino protecting and $R^1$ side chain amino protecting group on lysine cannot be the same;

$R^2$ is selected from the lysine protecting groups defined by $R^1$.

$R^3$, $R^4$ and $R^5$ are protecting groups for the alcoholic hydroxyl group of threonine and serine and is selected from the class consisting of acetyl, benzoyl, tert-butyl, trityl, benzyl, 2,6-dichlorobenzyl and benzyloxycarbonyl. The preferred protecting group is benzyl; or $R^3$, and/or $R^4$ and/or $R^5$ is hydrogen which means there is no protecting group on the alcoholic hydroxyl function;

$R^6$ is selected from the class consisting of OH, boxyl protecting group, if one is present and (2) remove any α-amino protecting group on the lysyl group on the N-terminal portion of the peptide. The $R^9$ carboxyl protecting group is illustrated by $C_1$–$C_6$ alkyl (e.g. methyl, ethyl, butyl, pentyl, isobutyl), benzyl, substituted benzyl (wherein the substituent is selected from at least one of nitro, methoxy and methyl e.g. p-methoxybenzyl, 2,4-dimethoxybenzyl, p-nitrobenzyl, 2,4,6-trimethylbenzyl), phenacyl, phthalimidomethyl, benzhydryl, trichloroethyl, 4-picolyl, β-methylthioethyl and 4-(methylthio) phenyl. The preferred $R^9$ group is benzyl.

The present invention also contemplates intermediates of the formula:

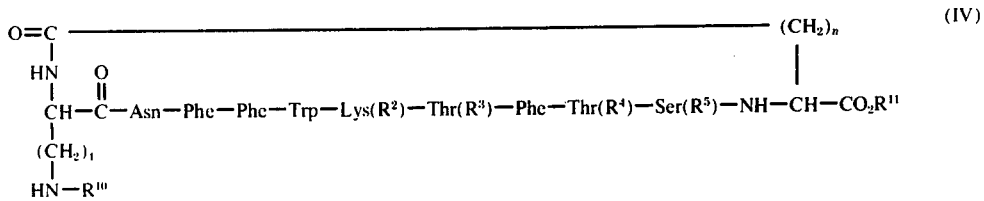

NHNH$_2$, N$_3$, OCH$_3$ and

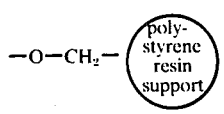

The polystyrene resin support is preferably a copolymer of styrene with about 1 to 2% divinyl benzene as a cross linking agent which causes the polystyrene polymer to be completely insoluble in certain organic solvents. The polystyrene polymer is composed of long alkyl chains bearing a phenyl ring on every second carbon and the terminal amino acid residue (Ser) is joined through a covalent carbon to carbon bond to these phenyl rings. The alkyl chains are cross linked at approximately every fiftieth carbon by p-diethylphenyl residues derived from divinyl benzene.

A further aspect of the present invention relates to novel undecapeptides of the formula:

wherein:
- $R^2$, $R^3$, $R^4$ and $R^5$ have the same meaning as in formula II;
- $R^{10}$ is a member selected from hydrogen and $R^1$; and
- $R^{11}$ is a member selected from the class consisting of hydrogen and $R^9$; with the proviso that at least one of $R^2$, $R^3$, $R^4$, $R^5$, $R^{10}$ and $R^{11}$ is other than hydrogen.

The novel decapeptides of formula II are prepared using solid phase synthesis. The synthesis is commenced from the C-terminal end of the peptide using an α-amino protected resin. Such a starting material can be prepared by attaching an α-amino protected serine to a chloromethylated resin or a hydroxymethyl resin. The preparation of the hydroxymethyl resin is described by Bodanszky et al., Chem. Ind. (London) 33, 1597–98 (1966). A chloromethylated resin is commercially available from Bio Rad Laboratories Richmond, Calif. and the preparation of such a resin is described by Stewart et al., "Solid Phase Peptide Synthesis" (Freeman & Co., San Francisco 1969), Chapter

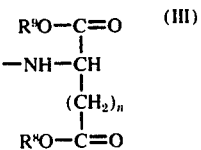

wherein:
$R^7$ is selected from the class consisting of hydrogen and an α-amino protecting group as defined by R;

$R^1$, $R^2$, $R^3$, $R^4$ and $R^5$ have the same meaning as set forth in connection with formula II;

$R^8$ is selected from the class consisting of hydrogen and a side chain carboxyl protecting group which is removed under conditions which will not remove the $R^9$ α-carboxyl protecting group. Thus $R^8$ and $R^9$ cannot be the same protecting group. Illustrative of $R^8$ side chain carboxyl protecting groups are t-butyl, benzhydryl and methyl;

$R^9$ is an α-carboxyl protecting group. The α-carboxyl protecting group represented by $R^9$ is one which is stable under conditions which (1) remove the $R^8$ car- 1, pp 1–6. The α-amino and side chain protected serine is coupled to the chloromethylated resin according to the procedure of Gisin, Helv. 56 p 1476 (1973). Following the coupling of the α-amino and side chain protected serine to the resin support, the α-amino protecting group is removed such as by using trifluoroacetic acid in methylene chloride, trifluoroacetic acid alone or HCl in dioxane. The deprotection is carried out at a temperature between about 0° C and room temperature. Other standard cleaving reagents and conditions for removal of specific α-amino protecting groups may be used as described in Schroder & Lubke, supra, 1 pp. 72–75. After removal of the α-amino protecting group the remaining α-amino protected amino acids are coupled step-wise in the desired order to obtain a compound of formula (II) or as an alternate to adding each amino acid separately to the synthesis, some of them may be coupled prior to addition to the solid phase reactor. The selection of an appropriate coupling reagent is within the skill of the art. A particularly suitable coupling reagent is N,N¹-diisopropyl carbodiimide. As previously indicated, the activating reagents used in the aforedescribed synthesis are those well known in the peptide art. Illustrative of these are (1) carbodiimides (e.g. N,N¹-dicyclohexycarbodiimide, N-ethyl N¹-(γ-dimethylamino propyl carbodiimide); (2) cyanamides (e.g. N,N-dibenzylcyanamide; (3) ketenimines; (4) isoxazolium salts (e.g. N-ethyl-5-phenyl isoxazolium-3¹-sulfonate; (5) monocyclic nitrogen containing heterocyclic amides of aromatic character containing one through four nitrogens in the ring such as imidazolides, pyrazolides, 1,2,4-triazolides. Specific heterocyclic amides that are useful include N,N¹-carbonyldiimidazole, N,N¹-carbonyl-di-1,2,4-triazole; (6) alkoxylated acetylene (e.g. ethoxyacetylene); (7) reagents which form a mixed anhydride with the carboxyl moiety of the amino acid (e.g. ethylchloroformate, isobutylchloroformate) and (8) nitrogen-containing heterocyclic compounds having a hydroxy group on one ring nitrogen (e.g. N-hydroxyphthalimide, N-hydroxysuccinimide, 1-hydroxybenzotriazole). Other activating reagents and their use in peptide coupling are described by Schroder & Lubke supra, in Chapter III and by Kapoor, J. Pharm. Sci., 59, pp 1–27, (1970).

Each protected amino acid or amino acid sequence is introduced into the solid phase reactor in about a fourfold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser et al., Analyt. Biochem, 34, 595 (1970).

After the desired amino acid sequence of formula II has been obtained the peptide is removed from the resin. This can be done by methanolysis to obtain a compound of the formula R-Lys($R^1$)-Asn-Phe-Phe-Trp-Lys($R^2$)-Thr($R^3$)-Phe-Thr($R^4$)-Ser($R^5$)-OCH$_3$ after which the C-terminal methyl ester is converted to the corresponding acid by hydrolysis followed by activation of the carboxyl group and formation of the hydrazide by classical methods of peptide synthesis to obtain a compound of formula III. However, the preferred procedure for obtaining a compound of formula I is in accordance with the reaction scheme shown in the flow diagram appended hereto. With reference to the flow diagram, a decapeptide linked to a resin of the formula R-Lys($R^1$)-Asn-Phe-Phe-Trp-Lys($R^2$)-Thr($R^3$)-Phe-Thr-($R^4$)-Ser($R^5$)-O-CH$_2$-polystyrene resin support (A) is converted to the corresponding hydrazide of the formula R-Lys($R^1$)-Asn-Phe-Phe-Trp-Lys($R^2$)-Thr($R^3$)-Phe-Thr($R^4$)-Ser($R^5$)-NHNH$_2$ (B) by reaction with hydrazine. The hydrazide of formula B is then converted to the corresponding azide of the formula R-Lys($R^1$)-Asn-Phe-Phe-Trp-Lys-($R^2$)-Thr($R^3$)Phe-Thr($R^4$)-Ser($R^5$)-N$_3$ (C) by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g. sodium nitrite, potassium nitrite) in the presence of a strong acid such as hydrochloric, phosphoric, sulfonic, etc. This reaction is carried out in the presence of either water and/or a non-aqueous solvent such as dimethylformamide, tetrahydrofuran, dioxane, chloroform, methylene chloride, etc., at a temperature between about −40° C and +20° C. The azide of formula C which is preferably not isolated from the reaction medium is then coupled with an amino acid of the formula

wherein $n$ is a whole number from 1 through 5; to obtain an undecapeptide of the formula:

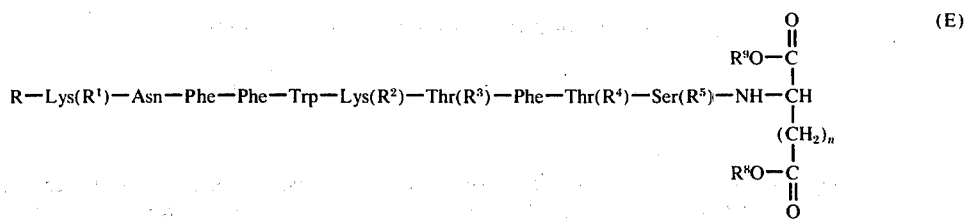

This coupling is carried out between a temperature of about −50° C and +50° C, preferably between about −25° C and +10° C.

The undecapeptide of formula (E) is then reacted with a cleaving reagent that will split off the α-amino protecting group on lysine as well as the $R^8$ carboxyl protecting group, if one is present to yield a compound of the formula

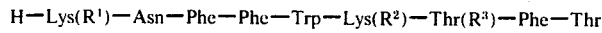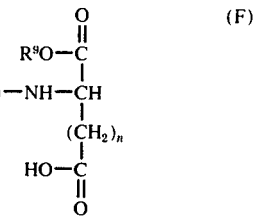

(F)

It is essential that the cleaving reagent be one which does not split off at this stage of the synthesis the $R^1$ and $R^2$ side chain amino protecting group on the lysyl amino acid residue in positions one and six of the undecapeptide nor the α-carboxyl protecting group represented by $R^9$. If these protecting groups were split off the desired cyclization of the next stage of the process would not occur. A particularly suitable cleaving reagent is trifluoroacetic acid where R is t-butyloxycarbonyl, $R^8$ is t-butyl, $R^1$ is 2-chlorobenzyloxycarbonyl and $R^9$ is benzyl. The selection of a compatible reagent for removal of various well known α-amino and side chain protecting groups is described by Schroder & Lubke, supra, 1 pp 72–75 the disclosure of which is incorporated herein by reference. While it is preferred that any side chain protecting groups represented by $R^2$, $R^3$, $R^4$ and $R^5$ not be split off during the formation of a compound of formula F, such groups can be cleaved, if desired so as to obtain a compound of the formula mixtures thereof. Other cyclization reagents may also be used as exemplified by the coupling reagents described supra in connection with the preparation of the decapeptide-resin as well as those described by Kopple, J. Pharm. Science, 61 pp. 1345–1356 (1972) the disclosure of which is incorporated herein by reference.

A compound of formula IV is then converted to a compound of formula I by cleaving the $R^1$ side chain amino protecting group as well as the $R^9$ α-carboxyl protecting group along with any protecting groups represented by $R^2$, $R^3$, $R^4$ and $R^5$. A particularly suitable cleaving system is hydrogen over a palladium catalyst. The cleavage step, if desired, can be carried out step wise by the selection of a reagent that will only cleave the $R^9$ α-carboxyl protecting group, followed by use of a reagent that will cleave the $R^1$ and any other side chain protecting groups. Alternatively the $R^1$ groups can be cleaved first followed by simultaneous or sequential cleavage of the other protecting groups including the $R^9$ group. The selection of suitable cleaving

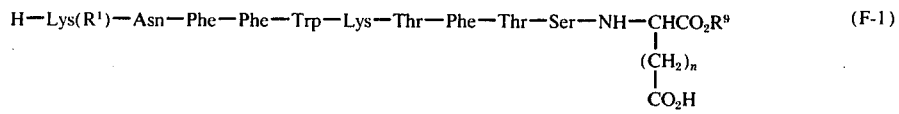

The compound of formula F is then cyclized to produce a compound of the formula reagents that are compatible with the particular side chain and α-carboxyl group that can be used are described by Schroeder and Lubke, supra, pp 72–75.

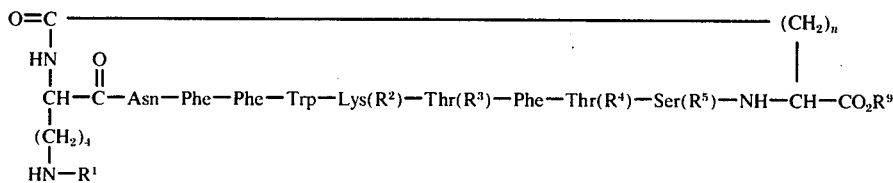

This cyclization is preferably carried out using N,N$^1$-dicyclohexylcarbodiimide (DCC) and N-hydroxybenzotriazole in the presence of an organic solvent in a temperature range between −40° C and +20° C. Suitable solvents include dimethylformamide, dichloromethane, chloroform, dioxane, tetrahydrofuran and An alternate route to preparing the compounds of formula (IV) is to convert a compound of the formula

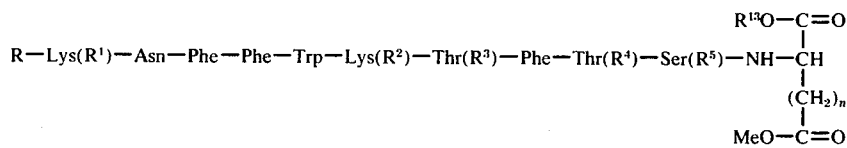

wherein $R^{13}$ is selected from the class consisting of hydrogen and $R^9$ and Me is methyl to the corresponding hydrazide by reaction with hydrazine to obtain R—Lys(R¹)—Asn—Phe—Phe—Trp—Lys(R²)—Thr(R³)—Phe—Thr(R⁴)—Ser(R⁵)—NH—CH(R¹³O—C=O)(CH₂)ₙ—C(=O)—NHNH₂

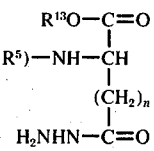

and thereafter converting this compound to the corresponding azide by reaction with a reagent that will yield nitrous acid in situ as previously described. The azide is then cyclized after first removing the α-amino protecting group on lysine.

The materials represented by formula D are known prior art materials and/or can be readily prepared by conventional techniques well known unprotected amino acids, namely aspartic acid, glutamic acid, α-aminoadipic acid, α-aminopimelic acid and α-aminosuberic acid. The preparation of these amino acids is described by Farkasova et al., Col. Czechoslov Chem. Commun. 30, 3117 (1965); The preparation of ω-carboxyl protected esters is described by Schroder et al., Annalen 673, pp 196, 208 (1964) and Rudinger et al., Col. Czechoslov. Chem. Commun. 32, 1229 (1967).

The following examples are illustrative of the preparation of the compounds of formulas of the present invention.

EXAMPLE 1

α-N-tert-butyloxycarbonyl-ε-2-chlorobenzyloxycarbonyl-L-lysyl-L-asparaginyl-L-phenylalanyl-L-phenylalanyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-hydroxymethyl polystyrene resin Chloromethylated polystyrene resin (Lab Systems, Inc.) 10 gr. is esterified with the cesium salt of Boc-Ser(Bzl)-OH (7.5 mmoles) as described by Gisin, Helv. 56, 1476 (1973). The amino acid resin is analyzed by quantitative amino acid analysis and is found to contain 0.40 mmoles serine per gram. This polymeric ester is treated according to schedule A for the incorporation of, Boc-Thr(Bzl)OH, Boc-Phe-OH, Boc-Thr(Bzl)-OH, Boc-Lys(ClZ)-OH, Boc-Trp-OH, Boc-Phe-OH, Boc-Phe-OH. The asparagine residue is introduced in the form of activated p-nitrophenyl ester, Boc-Asn-ONP, according to schedule B and finally Boc-Lys(ClZ)-OH according to schedule A.

Schedule A

1. The polymeric ester Boc-Ser(Bzl)-O-Resin, 10 gr equivalent to 4 mmoles serine/gr. is treated as follows:
2. Wash with CH₂Cl₂ three times.
3. Treat with trifluoroacetic acid CH₂Cl₂-dithioerythritol (1:1:0.5%) for 5 minutes
4. Treat with trifluoroacetic acid CH₂Cl₂ dithioerythritol (1:1:0.5%) for 25 minutes
5. Wash with CH₂Cl₂ three times
6. Wash with dimethylformamide
7. Treat with 12% triethylamine in dimethylformamide two times for 3 minutes.
8. Wash with dimethylformamide.
9. Wash with CH₂Cl₂ three times
10. Treat with 20 mmoles of the corresponding derivative of amino acid dissolved in CH₂Cl₂-dimethylformamide and stir for 5 minutes
11. Add in two portions 25 mmoles diisopropylcarbodiimide over a period of 30 minutes. Reaction time 18 hours.
12. Wash with dimethylformamide
13. Wash with CH₂Cl₂ three times
14. Test ninhydrin reaction according to Kaiser et al., Anal. Biochem, 34 595 (1970). In case of incomplete reaction repeat lines 10 to 14 as above.

Schedule B

1. The peptidoresin (in this example, Boc-Phe-Phe-Trp-Lys(ClZ)-Thr(Bzl)-Phe-Thr(Bzl)-Ser(Bzl)-O-Resin) is treated as follows:
2. Wash with CH₂Cl₂ three times
3. Treat with trifluoroacetic acid-CH₂Cl₂- dithioerythritol (1:1:0.5%) for 5 minutes
4. Treat with trifluoroacetic acid -CH₂Cl₂-dithioerythritol (1:1:0.5%) for 25 minutes
5. Wash with CH₂Cl₂ three times
6. Wash with dimethylformamide
7. Treat with 12% triethylamine in dimethylformamide × 2 for 3 minutes
8. Wash with dimethylformamide
9. Wash with CH₃Cl₃ three times
10. Treat with 40 mmoles of Boc-Asn-ONP in the presence of 2–3 drops gl. AcOH and dissolved in dimethylformamide. Reaction time 72 hours.
11. Wash with dimethylformamide three times
12. Wash with CH₂Cl₂ three times
13. Treat ninhydrin reaction The above titled peptidoresin, Boc-Lys(ClZ)-Asn-Phe-phe-Trp-Lys(ClZ)-Thr(Bzl)-Phe-Thr(Bzl)-ser(Bzl)-o-Resin is hydrolyzed and analyzed.

The D-Trp⁵ analogue is prepared by the same procedure except that Boc-D-tryptophan is substituted for Boc-L-tryptophan.

EXAMPLE 2

α-Butyloxycarbonyl-ε-2-chlorobenzyloxycarbonyl-L-lysyl-L-asparaginyl-L-phenylalanyl-L-phenylalanyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-hydrazide The peptide-resin Boc-Lys(ClCbz)-Asn-Phe-Phe-Trp-Lys (ClCbz)Thr(Bzl)-Phe-Thr(Bzl)-Ser(Bzl)-O-Resin (10 g.) of Example 1 is mixed with 75 ml. dimethylformamide and then with 10 ml. hydrazine (95% plus, grade) and the mixture stirred overnight.

The mixture is filtered, the solid part is washed with some more dimethylformamide and the combined filtrates are evaporated to a small volume. The residue is treated with excess water to afford a solid which is dissolved in some dimethylformamide and precipitated again with water, yield: 2.8 g. Amino acid analysis: Asp (1) 0.84, Thr (2) 1.62, Ser (1) 0.56, Phe (3) 3, Lys (2) 2.02, NH₃, Trp, not determined.

The D-Trp⁵ analogue is prepared by the same procedure.

EXAMPLE 3

α-Butyloxycarbonyl-ε-2-chlorobenzyloxycarbonyl-L-lysyl-L-asparaginyl-L-phenylalanyl-L-phenylalanyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-α-benzyl-ε-tert-butyl-l-glutamate The hydrate, Boc-Lys(ClCbz)-Asn-Phe-Phe-Trp-Lys(ClCbz)-Thr-(Bzl)-Phe-Thr(Bzl)-Ser(Bzl)-NHNH₂ (1.95 g., 1 mmole) of Example 2 is dissolved in dimethylformamide (ca. 50 ml.) cooled to −20° C. and treated with HCl/EtOAc (4.7 N, 0.6 ml.) followed by isoamyl nitrite (0.2 ml). The solution is stirred for 10 minutes at −20° C. then made alkaline with NEt₃ (0.6 ml.). To this solution H-Glu (O-tert-Bu)-OBzl (0.3 gr.) is added and stirred at −20° C. for one hour then at 0° C. for four days. The mixture is evaporated to dryness in vacuo and the residue is triturated with excess water to afford a white solid which is washed on the filter with 10% citric acid and water. Yield, 1.9 gr.

Amino acid analysis: Asp (1) 1.01, Thr (2) 1.73, Ser (1) 0.68, Glu (1) 0.84, Phe (3) 3, Lys (2) 2.1, NH₃, Trp, not determined.

The corresponding D-Trp⁵ containing analogue is coupled with H-Glu(O-tert-Bu)-O-Bzl by the same procedure.

Amino acid analysis: Asp (1) 1.14, Thr (2) 2.10, Ser (1) 0.71, Glu (1) 1.26, Phe (3) 3, Lys (2) 1.74, NH₃ (1) 2.72, Trp, not determined.

EXAMPLE 4

ε-2-Chlorobenzyloxycarbonyl-L-lysyl-L-asparaginyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-α-benzyl-L-glutamate The protected undecapeptide Boc-Lys(ClCbz)-Asn-Phe-Phe-Trp-Lys(ClCbz)-Thr(Bzl)-Phe-Thr(Bzl)-Ser(Bzl)-Glu(O-tert-Bu)-OBzl (1.8 gr) of Example 3 is mixed with 3 ml anisole and treated with 50 ml. TFA for 30 minutes at room temperature. The solution is evaporated to dryness in vacuo and the residue is flushed twice with ether. The residue is triturated with ether and the solid is dissolved in some dimethylformamide. This solution is poured into 100 ml. of a solution of NH₄OAc in water adjusted to pH 6.5. The white solid which precipitates is collected and dried to yield 1.35 g. of the above-identified material.

Amino acid analysis: Asp (1) 1.02, Thr (2) 1.64, Ser (1) 0.66, Glu (1) 0.80, Phe (3) 3, Lys (2) 1.99, NH₃ (1) 1.74, Trp, not determined.

The D-Trp⁵ analogue is partially deprotected in the same manner.

EXAMPLE 5

L-lysyl-L-asparaginyl-L-phenylalanyl-L-phenylalanyl-L-tryptophyl-L-lysyl-L-threonyl-L-phenylalanyl-L-threonyl-L-seryl-L-glutamyl (cyclo α-lysyl to γ-glutamyl) peptide The undecapeptide, H-Lys(ClCbz)-Asn-Phe-Phe-Trp-Lys (ClCbz)-Thr(Bzl)-Phe-Thr(Bzl)-Ser(Bzl)-Glu(OH)OBzl (1.1 g.) of Example 4 is dissolved in 250 ml. dimethylformamide and 100 ml. CH₂Cl₂ mixed with N-hydroxybenzotriazole (1.3 g.) cooled in an ice-bath and treated with DCC (0.5 g.) for two hours in the cold then for 30 hours at room temperature.

The mixture is evaporated to dryness, the residue is triturated with water to give a precipitate which is washed with aq-KHCO₃, water, 10% aq-citric acid, water and dried. The dry solid material is digested with abs. EtOH in the steam bath allowed to reach room temperature and filtered. The solid on the filter (570 mg.) is suspended in AcOH—H₂O (100 ml., 1:1) mixed with 10% Pd-C (100 mg.) and hydrogenated for 20 hours. The catalyst is removed and the filtrate is evaporated to dryness then taken in dilute aqueous AcOH and lyophilized to yield 82 mg. of a powder which is the above identified product.

$R_f$ (n-butanol-water-gl. acetic acid, 4.5:1): 0.60

$R_f$ (n-butanol-water-gl. acetic acid-pyridine, 30:24:6:20): 0.70

Amino acid analysis: Asp (1) 0.97, Thr (2) 1.84, Ser (1) 0.73, Glu (1) 0.89, Phe (3) 3, Lys (2) 1.91, NH₃, Trp, not determined.

EXAMPLE 6

L-Lysyl-L-asparaginyl-L-phenylalanyl-L-phenylalanyl-D-tryptophyl-L-lysyl-L-threonyl-L-phenylalanyl-L-threonyl-L-seryl-glutamyl-(cyclo-α-lysyl to γ-glutamyl)peptide The partially deprotected undecapeptide of the last paragraph of Example 4 (3 g.) was dissolved in DMF (36 ml.) and CH₂Cl₂ (322 ml.) and then triethylamine (0.2 ml.) was added to bring the pH to 7. N-Hydroxybenzotriazole (1 gm.) was added and the mixture was cooled in an ice-bath then treated with DCC (0.59 g.) for two days and under stirring. The reaction mixture was filtered and the filtrate was evaporated to a small volume. An excess of water was added to give a white solid which was filtered, washed with water and dried over P₂O₅. Yield 2.5 g.

The cyclic, partially protected undecapeptide (2 g.) was then treated with liquid hydrogen fluoride (ca. 100 ml.) in the presence of anisole (5 ml.) and in exclusion of air for 35 minutes in an ice-bath. The excess HF was removed in vacuo as fast as possible, the residue was taken up in 2M-aqueous AcOH and the aqueous phase was extracted with diethyl ether to remove the anisole. The aqueous solution was lyophilized to yield 1.03 g. of solid. This crude material (1 g.) was applied to a column of Sephadex G-25 (2.5 × 120 cm. and eluted with 2M-aqueous AcOH Fractions (4 ml. each) which emerged in tubes 89–109 were pooled and lyophilized to yield 155.8 mg. of a fluffy solid. This solid was applied to a column of Sephadex G 10 (1.5 × 50 cm.) and eluted. The eluate in tubes 13–35 was pooled and lyophilized to yield the title compound, 111.9 mg. $[\alpha]_D^{26}$ −30 (0.5, 75% aq.AcOH). Thin layer chromatography, Avicel plates (n-Butanol-water-acetic acid, 4:1:1) 0.47, (n-Butanol-water-acetic acid-pyridine, 30:24:6:20)0.71.

Amino acid hydrolysis: Asp (1) 1.02, Thr (2) 1.96, Ser (1) 0.92, Glu (1) 0.99, Phe (3) 3.12, Lys (2) 2, NH₃ (1) 1.16, Trp (1) 0.77.

The growth hormone activities of the compounds of Example 5 was determined by injecting rats weighing about 200–250 g. first with nembutal intraperitoneally at a dose of 50 mg/kg then after 5 minutes injecting the rats subcutaneously with a solution of the compound of Example 5 in saline at a dose of 2 mg/kg per rat. Blood samples are taken 15 minutes after injection with the compound of Example 5 and the growth hormone level determined by radioimmunoassay. The average growth hormone level in the control rats (13 animals) was found to be 132 ± 20 ng/ml whereas the growth hormone level in the rats (13 animals) given the compound of Example 5 was found to be 79 ± 14 ng/ml. The foregoing experiment was repeated but the dose of the compound of Example 5 was raised to 2.38 mg/kg and the blood was sampled 2 hours after injection. The average growth hormone level in the control rats (15 animals) was found to be 244 ± 38 ng/ml whereas the growth hormone level in the rats (15 animals) given the compound of Example 5 was found to be 89 ± 23 ng/ml.

Following the same procedure, the activity of the product of Example 6 was determined two hours after administration of 1,500 µg/kg to result in a growth hormone level of 18 ± 4 nanograms per milliliter with a control group level of 180 ± 27 nanograms per milliliter and after four hours, 34 ± 11 nanograms per milliliter with the control group level at 182 ± 49 nanograms per milliliter.

The finding at the two hour level of a substantial reduction in growth hormone level indicates that the compounds of formula I have surprisingly substantially long lasting activity than somatostatin which is reported by Brazeau et al., Biochem. and Biophys. Res. Comm. 60, p. 1202 (1974) to have a biological half life of about four minutes.

Another test was conducted with the compound of Example 5 to determine its effect upon insulin and glucagon levels. The in vivo assay determining simultaneous release of growth hormone, insulin and glucagon was carried out by injecting three groups of male rats weighing about 200 to 250 g. (9 animals per group) with pentobarbital intraperitoneally at a dose of 50 mg/kg per rat followed 15 minutes later by a subcutaneous injection of the compound of Example 5 at a dose of 2.7 mg/kg to one group of rats, a subcutaneous injection of SRIF at a dose of 0.2 mg/kg to another group of rats and a subcutaneous injection of saline solution to the third group of rats. Ten minutes after such injection the rats receive 150 mg. arginine in 0.5 ml. saline directly in the heart. Five minutes later the rats are decapitated, the blood collected and various radioimmunoassays are run. The results indicated that neither glucagon nor insulin levels were lowered by the administration of the compound of Example 5 whereas levels of these two hormones were lowered by somatostatin.

In an analogous manner, the product of Example 6 was tested in three separate experiments, with the following results in which "nd" means not determined:

| | Compound | Dose µg/kg | GH ng/ml | Insulin µU/ml | Glucagon picog/ml |
|---|---|---|---|---|---|
| 1. | control | | 247±52 | 194±17 | nd |
| | Example 6 | 3,000 | 61±7 | 152±13 | nd |
| 2. | control | | 315±22 | nd | nd |
| | Example 6 | 12 | 192±29 | nd | nd |
| 3. | control | | nd | 183±19 | 129±9 |
| | Example 6 | 3,000 | nd | 93±9 | 107±9 |

The compound of formula I described herein may be administered to warm blooded mammals, including humans, either intravenously, subcutaneously, intramuscularly or orally to inhibit the release of growth hormone where the host being treated requires therapeutic treatment for excess secretion of somatotropin which is associated with conditions such as acromegaly. The contemplated dose range for oral administration in tablet or capsule form to large mammals is about 0.015 mg to about 7 mg/kg of body weight per day while the dose range for intravenous injection in an aqueous solution is about 0.14 µg to about 0.15 mg/kg of body weight per day. When administered subcutaneously or intramuscularly a dose range of about 1.5 µg to about 7 mg/kg of body weight per day is contemplated. Obviously, the required dosage will vary with the particular condition being treated, the severity of the condition and the duration of treatment.

If active ingredient is administered in tablet form the tablet may contain: a binder such as gum tragacanth, corn starch, gelatin, an excipient such as dicalcium phosphate; a disintegrating agent such as corn starch, alginic acid, etc.; a lubricant such as magnesium stearate; and a sweetening and/or flavoring agent such as sucrose, lactose, wintergreen, etc. Suitable liquid carriers for intravenous administration include isotonic saline, phosphate buffer solutions, etc.

FLOW DIAGRAM

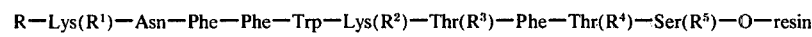

R—Lys($R^1$)—Asn—Phe—Phe—Trp—Lys($R^2$)—Thr($R^3$)—Phe—Thr($R^4$)—Ser($R^5$)—O—resin  (A)

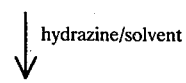

hydrazine/solvent

R—Lys($R^1$)—Asn—Phe—Phe—Trp—Lys($R^2$)—Thr($R^3$)—Phe—Thr($R^4$)—Ser($R^5$)—NHNH$_2$  (B)

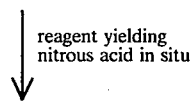

reagent yielding nitrous acid in situ

R—Lys($R^1$)—Asn—Phe—Phe—Trp—Lys($R^2$)—Thr($R^3$)—Phe—Thr($R^4$)—Ser($R^5$)—N$_3$  (C)

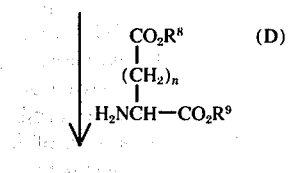

$$\begin{array}{c} CO_2R^8 \\ | \\ (CH_2)_n \\ | \\ H_2NCH—CO_2R^9 \end{array}$$  (D)

FLOW DIAGRAM-continued

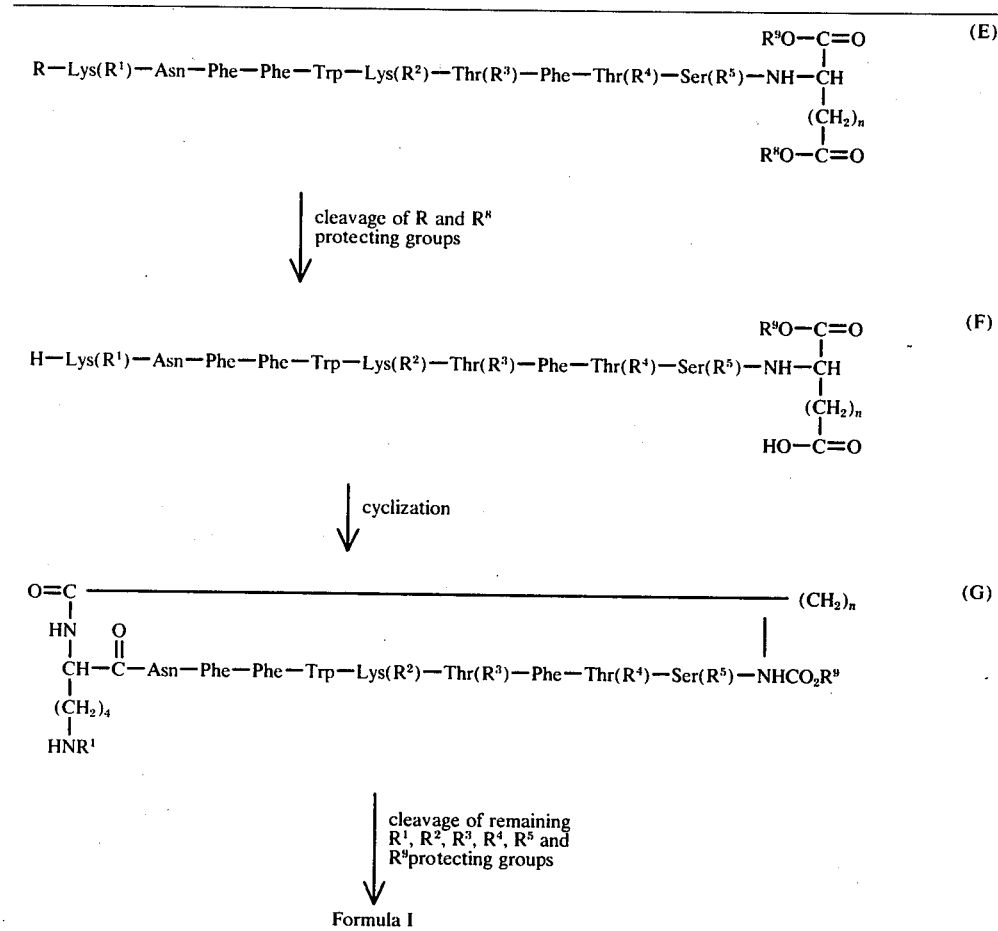

What is claimed is:
1. A compound selected from the class consisting of

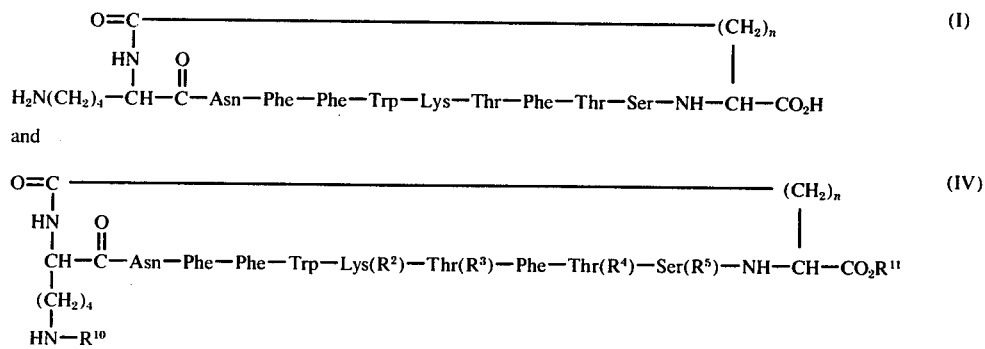

and the non-toxic acid salts thereof, wherein Trp represents either D- or L- tryptophyl and all the other amino acids are of the L-configuration;

$R^2$ is selected from the class consisting of a protecting group for the side chain amino substituent selected from benzyloxycarbonyl, tosyl, t-amyloxycarbonyl, t-butyloxycarbonyl, diisopropylmethoxycarbonyl and substituted benzyloxycarbonyl wherein said substituent is selected from halo and nitro;

$R^3$, $R^4$ and $R^5$ are selected from the class consisting of hydrogen and a protecting group for the alcoholic hydroxyl group of threonine and serine selected from acetyl, benzoyl, tert-butyl, trityl, benzyl, 2,6 dichlorobenzyl and benzyloxycarbonyl;

$R^{10}$ is selected from the class consisting of hydrogen and a protecting group for the amino function selected from those defined by $R^2$;

$R^{11}$ is selected from the class consisting of hydrogen and an α-carboxyl protecting group selected from $C_1$–$C_6$ alkyl, benzyl, substituted benzyl, phenacyl, phthalimidomethyl, benzhydryl, trichloroethyl, 4-picolyl, β-methylthioethyl, 4-(methylthio)phenyl, said substituent on benzyl being selected from nitro, methyl and methoxy; and $n$ is a whole number from 1 through 5; and wherein at least one of $R^2$, $R^3$, $R^4$, $R^5$, $R^{10}$ and $R^{11}$ is other than hydrogen.

2. A compound according to claim 1 where n is two.
3. A compound according to claim 1 wherein Trp is D-tryptophyl.
4. A compound according to claim 1 wherein Trp is L-tryptophyl.
5. A compound according to claim 1 wherein $R^2$ and $R^{10}$ are 2-chlorobenzyloxycarbonyl, $R^3$, $R^4$ and $R^5$ are benzyl, and $R^{11}$ is benzyl.
6. A compound of the formula

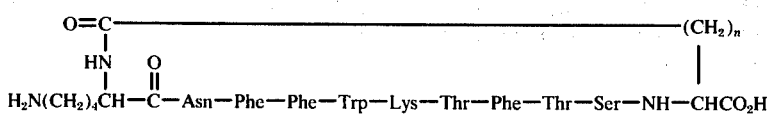

and its non-toxic salts, wherein n is a whole number from 1 through 5; and all chiral amino acids in said compound being of the L-configuration, except for Trp, which is of the D- or L-configuration.

7. A compound according to claim 6 which is selected from L-lysyl-L-asparaginyl-L-phenylalanyl-L-phenylalanyl-L-tryptophyl-L-lysyl-L-threonyl-L-phenylalanyl-L-threonyl-L-seryl-L-glutamyl (cyclo-α-lysyl to γ-glutamyl)peptide and a non-toxic salt thereof.

8. A compound according to claim 6 which is selected from L-lysyl-L-asparaginyl-L-phenylalanyl-L-phenylalanyl-D-tryptophyl-L-lysyl-L-threonyl-L-phenylalanyl-L-threonyl-L-seryl-L-glutamyl (cyclo α-lysyl to γ-glutamyl)peptide and a non-toxic salt thereof.

9. A compound of the formula

R-Lys($R^1$)-Asn-Phe-Phe-Trp-Lys($R^2$)-Thr($R^3$)-Phe-Thr($R^4$)-Ser($R^5$)-$R^6$

III wherein Trp represents either D- or L-tryptophyl and all other chiral amino acids are of the L-configuration;
R is an α-amino protecting group that is cleavable under conditions that will not cleave the $R^1$ and $R^2$ protecting group;
$R^1$ and $R^2$ is a protecting group for the side chain amino substituent of lysine selected from the class consisting of benzyloxycarbonyl, tosyl, t-amyloxycarbonyl, t-butyloxycarbonyl, diisopropylmethoxycarbonyl and substituted benzyloxycarbonyl, said substituent selected from halo and nitro and said $R^1$ and $R^2$ group not being the same as said R group;
$R^3$, $R^4$ and $R^5$ are selected from the class consisting of hydrogen and a protecting group for the alcoholic hydroxyl group of threonine and serine selected from acetyl, benzoyl, tert-butyl, trityl, benzyl, 2,6 dichlorobenzyl and benzyloxycarbonyl; and
$R^6$ is selected from the class consisting of OH, $NHNH_2$, $N_3$, $OCH_3$ and

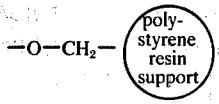

10. A compound according to claim 9 wherein R is tert-butyloxycarbonyl, $R^1$ and $R^2$ are 2-chlorobenzyloxycarbonyl and $R^3$, $R^4$ and $R^5$ are benzyl.
11. A compound according to claim 10 wherein $R^6$ is $NHNH_2$.
12. A compound according to claim 10 wherein $R^6$ is

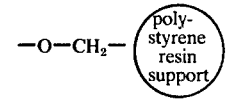

13. A compound selected from those of the formula

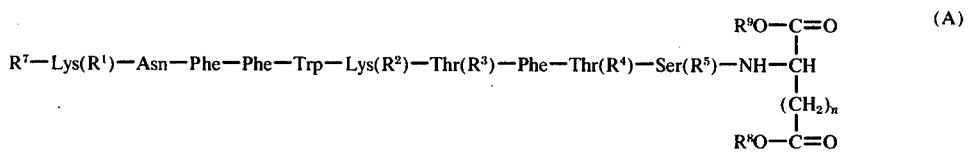

and

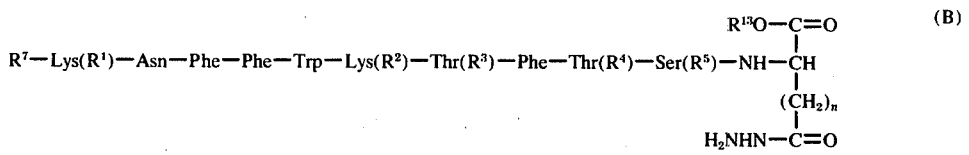

wherein Trp represents either D- or L-tryptophyl and all other chiral amino acids are of the L-configuration;
$R^1$ and $R^2$ is a protecting group for the side chain amino substituent of lysine selected from the class consisting of benzyloxycarbonyl, tosyl, t-amyloxycarbonyl, t-butyloxycarbonyl, diisopropylmethoxycarbonyl and substituted benzyloxycarbonyl, said substituent being selected from halo and nitro;
$R^3$, $R^4$ and $R^5$ are selected from the class consisting of hydrogen and a protecting group for the alcoholic hydroxyl group of threonine and serine selected from acetyl, benzoyl, tert-butyl, trityl, benzyl, 2,6 dichlorobenzyl and benzyloxycarbonyl;
$R^7$ is selected from the class consisting of hydrogen and an α-amino protecting group, said α-amino protecting group being different from said $R^1$ and $R^2$ protecting group and said α-amino protecting group being cleavable under conditions that will not cleave said $R^1$ and $R^2$ protecting group;
$R^8$ is selected from the class consisting of hydrogen and a side chain carboxyl protecting group which is removable under conditions that will not remove the $R^9$ carboxyl protecting group;

$R^9$ is an α-carboxyl protecting group which is stable under reaction conditions which cleave said $R^7$ and $R^8$ protecting groups, said α-carboxyl protecting group being selected from the class consisting of $C_1$–$C_6$ alkyl, benzyl, phenacyl, phthalimidomethyl, benzhydryl, trichloroethyl, 4-picolyl, β-methylthioethyl, 4-(methylthio) phenyl and substituted benzyl, said substituent being selected from the class consisting of nitro, methoxy and methyl;

$R^{13}$ is selected from the class consisting of hydrogen and a protecting group selected from those defined by $R^9$; and $n$ is a whole number from 1 through 5.

14. A compound according to claim 13 represented by formula A wherein $R^1$ and $R^2$ are 2-chlorobenzyloxycarbonyl, $R^3$, $R^4$ and $R^5$ are benzyl, $R^7$ is t-butyloxycarbonyl, $R^8$ is t-butyl and $R^9$ is benzyl.

15. A compound according to claim 13 represented by formula A wherein $R^1$ and $R^2$ are 2-chlorobenzyloxycarbonyl, $R^3$, $R^4$ and $R^5$ are benzyl, $R^7$ is hydrogen, $R^8$ is hydrogen and $R^9$ is benzyl.

* * * * *